(12) United States Patent
Järvinen et al.

(10) Patent No.: US 7,384,180 B2
(45) Date of Patent: Jun. 10, 2008

(54) METHOD AND APPARATUS FOR MANUFACTURING CONCRETE MASS

(75) Inventors: Lassi Antero Järvinen, Valkeakoski (FI); Aulis Käppi, Parainen (FI)

(73) Assignee: Consolis Technology Oy AB, Vantaa (FI)

(*) Notice: Subject to any disclaimer, the term of this patent is extended or adjusted under 35 U.S.C. 154(b) by 439 days.

(21) Appl. No.: 11/000,432

(22) Filed: Dec. 1, 2004

(65) Prior Publication Data

US 2005/0141338 A1 Jun. 30, 2005

(30) Foreign Application Priority Data

Dec. 31, 2003 (FI) .................................. 20031930

(51) Int. Cl.
*B28C 7/00* (2006.01)
*G01N 11/00* (2006.01)
*G01N 11/14* (2006.01)

(52) U.S. Cl. ............................ 366/2; 366/64; 366/142; 366/601; 73/54.02; 73/54.03

(58) Field of Classification Search ................ 366/200, 366/2, 64, 142, 241, 348, 601; 73/54.03, 73/54.02
See application file for complete search history.

(56) References Cited

U.S. PATENT DOCUMENTS

| 2,089,604 | A | * | 8/1937 | Hagy ........................... 366/15 |
| 2,339,991 | A | * | 1/1944 | Hagy ......................... 73/54.35 |
| 2,342,749 | A | * | 2/1944 | Maxon, Jr. .................. 73/54.03 |
| 2,643,542 | A | * | 6/1953 | Cronk ........................ 73/54.03 |
| 3,731,909 | A | * | 5/1973 | Johnson ........................ 366/61 |
| 4,027,859 | A | * | 6/1977 | Stone .......................... 366/142 |
| 4,281,288 | A | * | 7/1981 | Izumi .......................... 324/772 |
| 4,318,177 | A | * | 3/1982 | Rapp et al. .................. 700/265 |
| 4,522,499 | A | * | 6/1985 | Hudelmaier ................. 366/56 |
| 4,544,275 | A | * | 10/1985 | Hudelmaier ................. 366/30 |
| 4,900,154 | A | * | 2/1990 | Waitzinger et al. ........... 366/56 |
| 5,541,855 | A | * | 7/1996 | Enzler et al. ................ 702/113 |
| 5,713,663 | A | * | 2/1998 | Zandberg et al. .............. 366/8 |
| 5,752,768 | A | * | 5/1998 | Assh .............................. 366/3 |
| 6,227,039 | B1 | * | 5/2001 | Te'eni ....................... 73/54.03 |
| 6,286,987 | B1 | * | 9/2001 | Goode et al. ................. 366/60 |
| 2005/0141338 | A1 | * | 6/2005 | Jarvinen et al. ............... 366/2 |

FOREIGN PATENT DOCUMENTS

| DE | 4020252 | | 5/1991 |
| DE | 19503028 | | 8/1996 |
| DE | 10054823 | * | 4/2002 |
| EP | 0126573 | * | 11/1984 |

(Continued)

*Primary Examiner*—Tony G Soohoo
(74) *Attorney, Agent, or Firm*—Buchanan Ingersoll & Rooney PC

(57) ABSTRACT

Method and apparatus for manufacturing concrete mass, the concrete mass being manufactured in a mixer, and the torque caused by the mixing of the concrete mass to the mixing elements used for mixing of the concrete mass and/or the power consumption of the drive of the mixer, being measured in said method. The torque caused to the mixing elements of the concrete mass and/or the power consumption of the drive is measured at least with two different mixing speeds, and based on the measurement results, the properties of the concrete mass are determined.

15 Claims, 2 Drawing Sheets

FOREIGN PATENT DOCUMENTS

Figure 1:
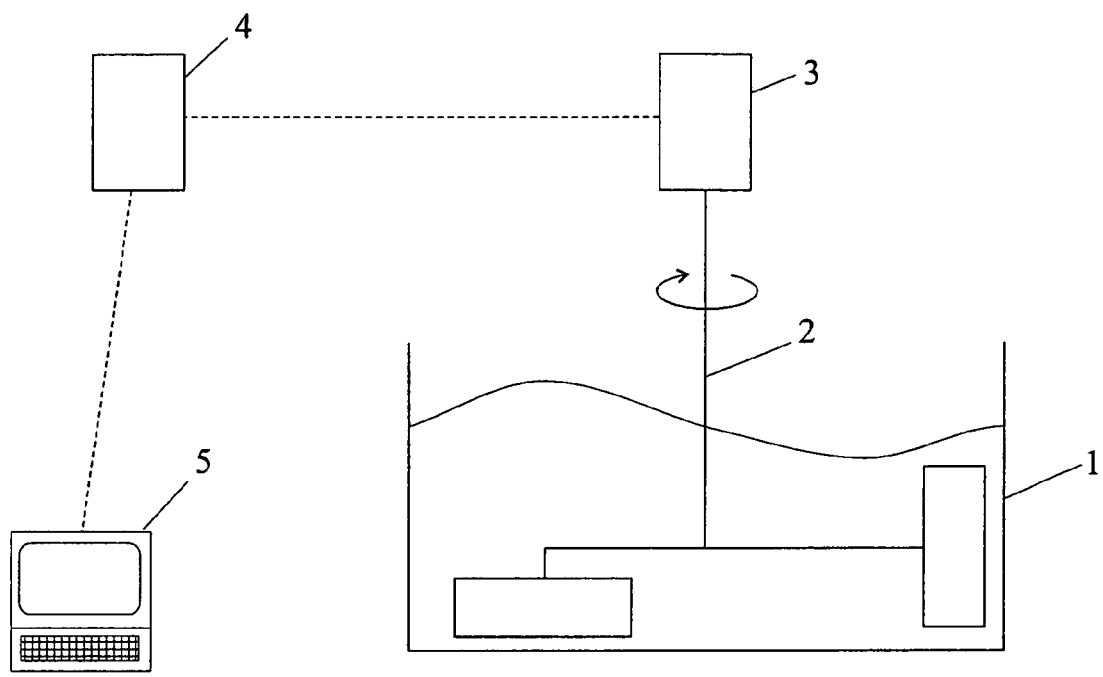

| | | |
|---|---|---|
| EP | 0 901 017 | 3/1999 |
| EP | 001550535 A1 * | 2/2005 |
| GB | 1182590 * | 2/1970 |
| GB | 2 144 240 | 2/1985 |
| GB | 2 147 215 | 5/1985 |
| GB | 2329027 * | 9/1997 |

* cited by examiner

METHOD AND APPARATUS FOR MANUFACTURING CONCRETE MASS

The present invention is related to manufacturing of concrete mass. More precisely, the invention is related to a method and apparatus for measurement and changing of the workability properties in the manufacturing process of the concrete mass.

BACKGROUND

Essential magnitudes describing the quality and properties of concrete mixture are the yield strength, toughness and air content of the mass, the yield strength being often described by means of slump. By using these magnitudes, the rheology of the concrete mass can be determined, which is of use for manufacturing concrete mass of suitable type for different casting processes and products.

The slump and air content of the concrete mass is measured traditionally by means of sampling from a concrete mass batch. For the measurement of the slump, generally a vessel (slump cone) is used, with open bottom and open top, conically narrowing upwards, to be located on a floor or on some other suitable surface. The slump cone is filled with fresh concrete mass in several batches, and between the adding of the batches, the concrete mass in the slump cone is compacted manually. After being filled up to its upper surface and compacted, the conical vessel around the concrete mass is removed from around the concrete mass, whereby the concrete mass is free to spread on its base. After that the difference between the height of the upper lever of the spread concrete mass heap and the initial situation, in other words, the height of the upper surface of the filled slump cone will be measured. This difference stands for the slump of the concrete mass.

Concrete rheometer is used for measuring the toughness of the concrete in research on the field of concrete.

The air content of the concrete mass is measured with a separate measuring device of the air content, said device being filled with a certain amount of fresh concrete mass and, after that, sealed and measured. The construction of the device, as well as the measuring method, is defined in the international standards of the field of concrete.

The methods used for measuring the slump and air content of concrete mass as described above, are slow, time consuming and difficult. In addition, the concrete rheometer necessary for the toughness measurement is expensive.

Attempts have been made to describe the properties of the concrete mass also by means of the power taken by the mixer. This power or moment of the normal mixing speed alone, however, does not describe the workability of the concrete with an adequate accuracy, because the mass flow in the casting process of the concrete takes place with low speed.

One way to determine and regulate the properties and workability of the concrete mass is to define the moisture content of the concrete mass. Thereby the properties of the concrete mass can be conditioned by adding either liquid or dry substances to the mix. This kind of a solution utilizing the measurement of moisture content, however, is not adequate or satisfactory, especially for the concrete masses, in which agents are used. In these masses, the combined effects of the agent and the concrete can lead to changes in the workability properties of the concrete, even if the moisture content of the mass is unchanged.

The patent publication U.S. Pat. No. 6,227,039 discloses a system and a method for controlling the concrete manufacturing, wherein the rheological properties of the concrete mass are measured and controlled. In the solution in accordance with said publication, a concrete mass is manufactured, and after that its workability and/or other magnitudes describing the necessary properties of the concrete mass are defined with a separate measuring device, and the manufacturing of the concrete mass will be controlled based on these test results.

DESCRIPTION OF THE INVENTION

With the present invention, a method and apparatus are provided, by means of which the drawbacks related to the prior art can be solved and a real time follow-up and conditioning of the properties of the concrete mass can be provided in the concrete manufacturing process.

In the solution in accordance with the present invention, the mixer of the concrete mass is used as a measuring device, whereby the concrete mass is mixed with several different speeds of rotation and the torque of the mixing motor is monitored. Based on the measurements performed with different speeds, the properties of the concrete mass can be determined and they can be changed with necessary measures, for instance by adding agents and the like, during the mixing.

More precisely, the method in accordance with the present invention is characterized by what is stated in the characterizing part of claim 1, and the apparatus in accordance with the invention is characterized by what is stated in the characterizing part of claim 5.

Figure 2:
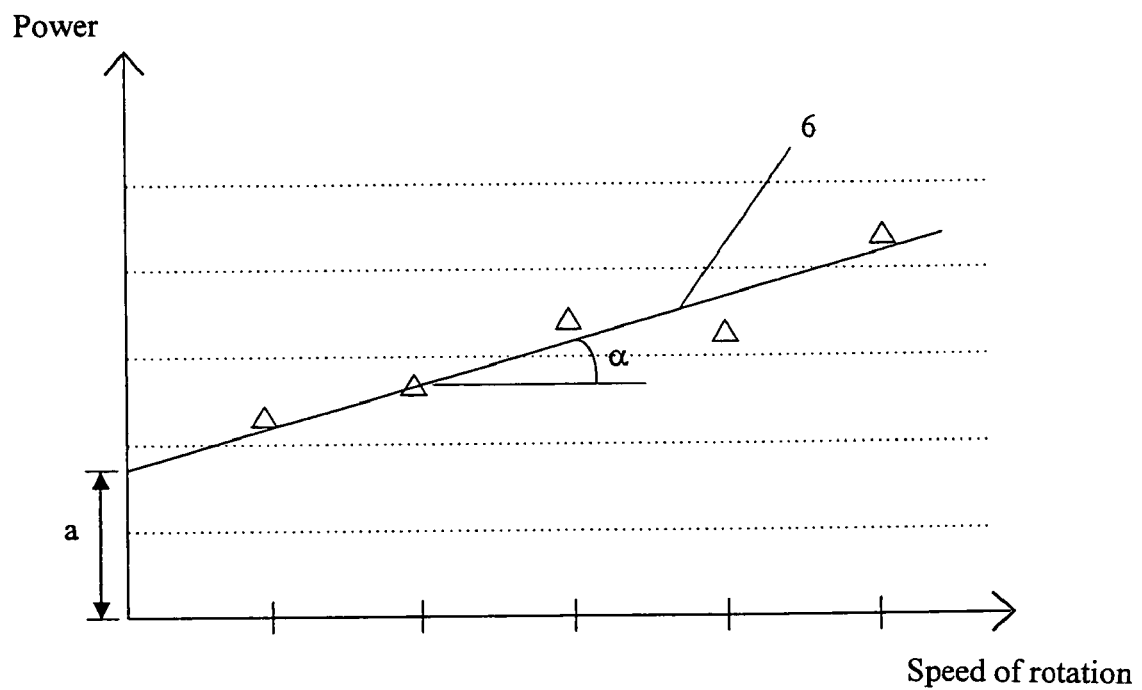

The invention will be described in more detail in the following, with reference to the enclosed drawing, wherein FIG. 1 shows a schematic drawing of one example of the apparatus in accordance with the invention, and FIG. 2 shows one example of utilizing the measurement results for determination of the properties of the concrete mass.

FIG. 1 shows schematically one example of the apparatus in accordance with the invention, comprising a mixing tank 1 of the concrete mass, mixing element 2, electric motor 3 driving the mixing element, frequency converter 4 and a computer 5.

The example shown in FIG. 1 of the solution in accordance with the invention is the following: the electric motor 3 driving the mixing element 2 of the mixing tank 1 is connected to a frequency converter 4. The frequency converter is controlled by means of a computer 5. When mixing the concrete mass with the apparatus, the mixing in the initial state is performed as usual. After the components of the mass to be mixed are blended enough, the torque of the motor is measured at that moment, for example with a measuring device included in the frequency converter, and the results of the measurement are transmitted to the computer. Next, the speed of rotation of the motor is decreased 20% and the torque of the motor is measured again. This will be repeated 3 times, in other words, the torque of the motor is measured with 100%, 80%, 60%, 40% and 20% speeds of rotation compared with the normal speed of rotation of the motor used for the mixing of the concrete mass.

The measured torques with different speeds of rotation are transmitted to the computer 5, for calculating, based on this data, an estimation of the workability properties of the concrete mass to be mixed, for example for yield strength, toughness or slump and air content. Based on these estimations, necessary measures can be taken, for example adding of material or agent to the concrete mass and changes of the mixing time for manufacturing concrete mass of the right quality for the casting process during the same mixing batch.

In the solution in accordance with the invention, also the power used by the motor of the mixer can be measured, instead of the measurement of the torque. The determination of the workability properties of the concrete mass based on the measurement of the power, however, is less accurate than that based on the measurement of the torque.

The measurement of the torque can advantageously also be performed as a stepless measurement when the speed of rotation of the mixer decreases to a certain percentage. In this way the time required by the measurement can be minimized in the manufacturing process of the concrete mass.

In the following, the calculation process by the computer 5 is described, with reference to FIG. 2. FIG. 2 shows a graph formed by the measurement described above with reference to FIG. 1.

In the graph of FIG. 2, the measurement results are shown as triangles. A graph 6 has been drawn in this case as a straight, based on these measurement results. The graph can also in some cases be curved. Based on the graph, the magnitudes a and α are determined, a being the distance of the graph from the x-axis at the point 0 of the x-axis and α being the slope of the graph. The value a calculated from the graph describes the yield value of the concrete mass and the angle α describes the toughness of the concrete mass.

By means of the a-value determined based on the measurements performed after the calibration of the measuring apparatus, the slump of the concrete mass can be calculated. The air content of the concrete mass can be calculated from α and a determined based on the performed measurements, as well as from some other magnitudes of the process, like for instance grain size, amounts of raw materials etc.

The apparatus in accordance with the invention can in the simplest way be implemented with a two-speed motor, whereby no separate frequency controller is needed for the adjustment of the motor speed in the apparatus. In that case, the measurement is implemented only with two different mixing speeds.

In the solution in accordance with the invention, the torque affecting the mixer can also be determined among others by measuring the power of the drive motor and by dividing it by the speed of rotation, by measuring the supporting force of the drive motor, by measuring the supporting force of the mixing tank, by means of the internal signal processing of the frequency converter, by measuring the phase shift of the current and voltage at the drive motor and/or with a torque sensor connected to the drive shaft of the motor or the gearbox.

The invention claimed is:

1. A method for manufacturing concrete mass, the method comprising:
    manufacturing concrete mass in a mixer apparatus, the mixer apparatus comprising a primary mixer adapted to manufacture a concrete mass, the primary mixer mixing the concrete mass with a mixing element, the primary mixer apparatus comprising a mixer drive motor;
    driving the mixing element at two different mixing speeds;
    respectively measuring the torque caused to the mixing element and/or the power consumption of the mixer drive motor at two or more different mixing speeds;
    using the measurement results to determine at least two properties of the concrete mass, wherein the at least two properties are selected from the group consisting of the slump of the concrete mass, the toughness and the air content of the concrete mass.

2. A method in accordance with claim 1, the method further comprising adding an amount of additional concrete material and/or agents, wherein the amount added is based on the determined properties, and/or changing the mixing time for the concrete mass, wherein the change in mixing time is based on the determined properties, in order to change the determined properties.

3. A method in accordance with claim 2, the mixer apparatus comprising a mixing tank of the concrete mass, a frequency converter, a drive shaft and a gearbox,
    wherein the torque is determined:
    by measuring the power of the drive motor and by dividing it by the speed of rotation of the drive motor;
    by measuring the supporting force of the drive motor;
    by measuring the supporting force of the mixing tank of the concrete mass;
    from internal signal processing of the frequency converter;
    by measuring the phase shift of the current and voltage at the drive motor and/or;
    from a torque sensor connected to the drive shaft of the drive motor or the gearbox.

4. A method in accordance with claim 1, wherein the torque and/or the power consumption of the mixer drive are continuously measured when the mixing speed changes steplessly between two different mixing speeds.

5. A method in accordance with claim 4, the mixer apparatus comprising a mixing tank of the concrete mass, a frequency converter, a drive shaft and a gearbox,
    wherein the torque is determined:
    by measuring the power of the drive motor and by dividing it by the speed of rotation of the drive motor;
    by measuring the supporting force of the drive motor;
    by measuring the supporting force of the mixing tank of the concrete mass;
    from internal signal processing of the frequency converter;
    by measuring the phase shift of the current and voltage at the drive motor and/or;
    from a torque sensor connected to the drive shaft of the drive motor or the gearbox.

6. A method in accordance with claim 4, the method further comprising adding an amount of additional concrete material and/or agents, wherein the amount added is based on the determined properties, and/or changing the mixing time for the concrete mass, wherein the change in mixing time is based on the determined properties, in order to change the determined properties.

7. A method in accordance with claim 1, the mixer apparatus comprising a mixing tank of the concrete mass, a frequency converter, a drive shaft and a gearbox,
    wherein the torque is determined:
    by measuring the power of the drive motor and by dividing it by the speed of rotation of the drive motor;
    by measuring the supporting force of the drive motor;
    by measuring the supporting force of the mixing tank of the concrete mass;
    from internal signal processing of the frequency converter;
    by measuring the phase shift of the current and voltage at the drive motor and/or;
    from a torque sensor connected to the drive shaft of the drive motor or the gearbox.

8. An apparatus for manufacturing concrete mass, the apparatus comprising:

a mixing tank of concrete mass;

a primary mixer adapted to manufacture a concrete mass;

elements for mixing the concrete mass;

a drive motor;

elements for changing the mixing seed of the mixing elements of the concrete mass;

elements for measuring the torque caused by the mixing of the concrete mass with the primary mixer andlor for measuring the power consumption of the drive motor of the primary mixer at two different seeds during manufacturing of the concrete mass and determining at least two properties of the concrete mass, wherein the at least two properties are selected from the group consisting of the slump of the concrete mass, the toughness and the air content of the concrete mass; and elements for determining the at least two properties of the concrete.

9. An apparatus in accordance with claim 8, wherein the apparatus comprises elements for processing the measurement results of the torque caused by the mixing of the concrete mass and/or of the power consumption of the drive motor of the mixer.

10. An apparatus in accordance with claim 9, wherein the elements for processing the measurement results of the torque caused by the mixing of the concrete mass and/or of the power consumption of the drive motor of the mixer comprise a computer.

11. An apparatus in accordance with claim 9, wherein the drive motor is an electric motor and the elements for changing the mixing speed of the mixing elements of the concrete mass comprise a frequency converter.

12. An apparatus in accordance with claim 9, wherein the drive motor is a two-speed motor.

13. An apparatus in accordance with claim 8, wherein the drive motor is an electric motor and the elements for changing the mixing speed of the mixing elements of the concrete mass comprise a frequency converter.

14. An apparatus in accordance with claim 13, wherein the elements for processing the measurement results of the torque caused by the mixing of the concrete mass and/or of the power consumption of the drive motor of the mixer comprise a computer.

15. An apparatus in accordance with claim 8, wherein the drive motor is a two-speed motor.

\* \* \* \* \*